(12) United States Patent
Tiensuu

(10) Patent No.: US 10,039,493 B2
(45) Date of Patent: Aug. 7, 2018

(54) SENSOR GUIDE WIRE ASSEMBLY WITH BUTTON-CELL TYPE BATTERY

(71) Applicant: ST. JUDE MEDICAL COORDINATION CENTER BVBA, Zaventem (BE)

(72) Inventor: Stefan Tiensuu, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 941 days.

(21) Appl. No.: 14/458,400

(22) Filed: Aug. 13, 2014

(65) Prior Publication Data

US 2016/0045164 A1 Feb. 18, 2016

(51) Int. Cl.
- *A61B 5/00* (2006.01)
- *A61B 5/07* (2006.01)
- *A61B 5/0215* (2006.01)
- *A61B 5/026* (2006.01)
- *H04B 13/00* (2006.01)

(52) U.S. Cl.
CPC .......... *A61B 5/6851* (2013.01); *A61B 5/0015* (2013.01); *A61B 2560/0214* (2013.01); *A61B 2560/045* (2013.01)

(58) Field of Classification Search
CPC .............................. A61B 5/6851; A61B 5/0015
See application file for complete search history.

(56) References Cited

U.S. PATENT DOCUMENTS

| | | | |
|---|---|---|---|
| 6,167,763 B1 | 1/2001 | Tenerz et al. | |
| 6,615,067 B2 | 9/2003 | Hoek et al. | |
| 7,998,089 B2 | 8/2011 | Smith | |
| 9,700,347 B2 * | 7/2017 | Shiber | A61B 17/320758 |
| 2005/0277851 A1 * | 12/2005 | Whittaker | A61M 25/0158 600/585 |
| 2006/0009817 A1 | 1/2006 | Tulkki | |
| 2006/0207335 A1 * | 9/2006 | Tenerz | A61B 5/0215 73/754 |
| 2009/0082678 A1 * | 3/2009 | Smith | A61B 5/0215 600/486 |

(Continued)

OTHER PUBLICATIONS

"Photographs of PressureWire™ Aeris™ Device" (6 pages).

*Primary Examiner* — Sean Dougherty
(74) *Attorney, Agent, or Firm* — Foley & Lardner LLP

(57) ABSTRACT

A sensor guide wire assembly having a button-cell type battery includes a transmitter unit configured to be connected to a sensor guide wire that is insertable into a patient to measure a parameter, the transmitter unit being configured to wirelessly transfer data representing the measured parameter to a communication unit. The transmitter unit includes a housing, a printed circuit board holder disposed in the housing, and a printed circuit board disposed in the housing and held by the printed circuit board holder. The printed circuit board includes a plurality of electrical contacts. A slider is slidable from a location outside the housing, the slider including a protrusion extending into an area inside the housing. A space within the housing is configured to hold one or more batteries. The slider is slidable from a first position, at which a micro-switch is not activated, to a second position, at which the micro-switch is activated by the protrusion of the slider, which allows power to be provided to the printed circuit board.

18 Claims, 6 Drawing Sheets

(56) References Cited

U.S. PATENT DOCUMENTS

2009/0124880 A1    5/2009   Smith
2010/0222661 A1*   9/2010   Von Malmborg ... A61B 5/0215
                                                                   600/372
2010/0268038 A1    10/2010   Smith

* cited by examiner

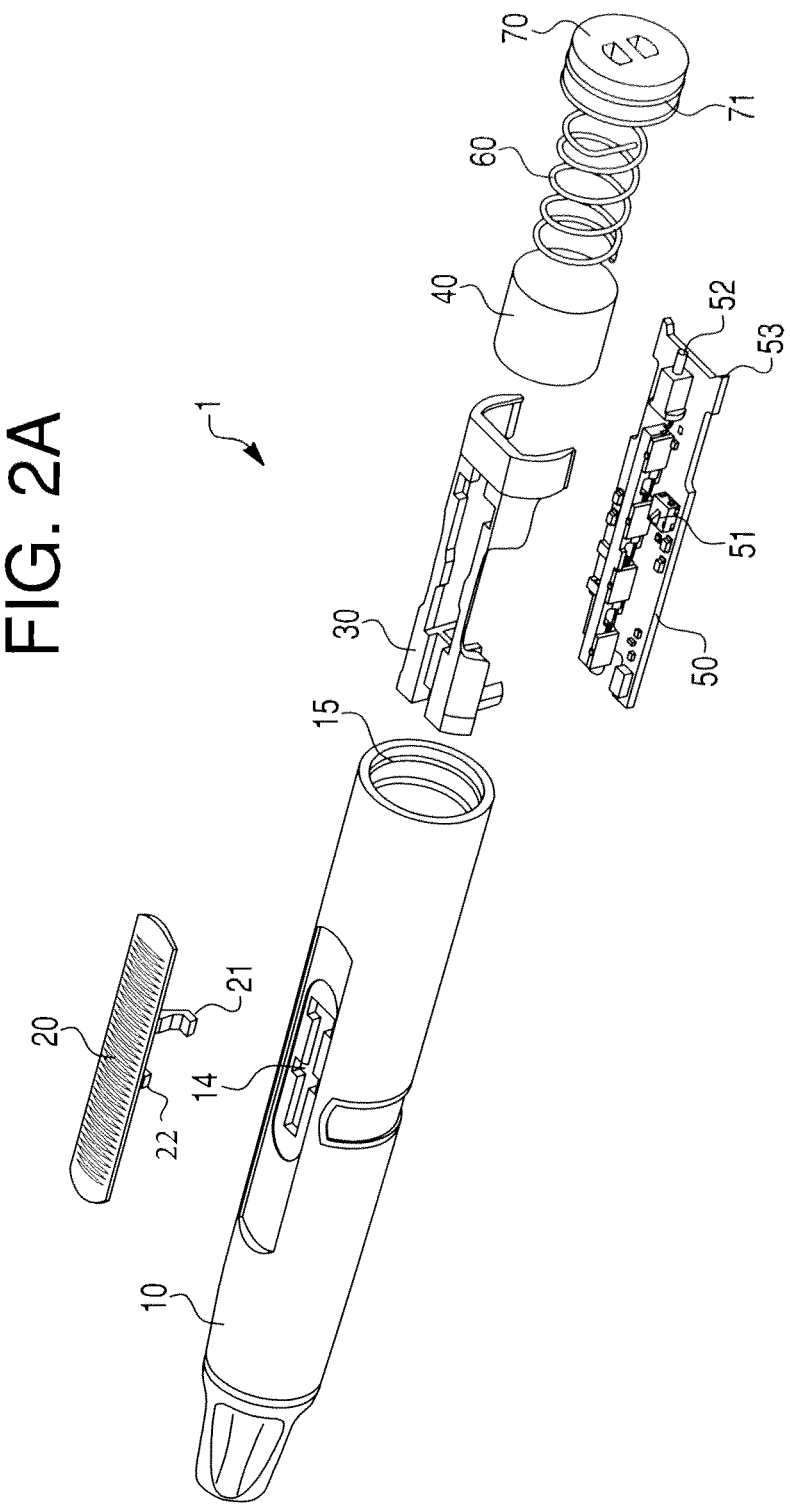

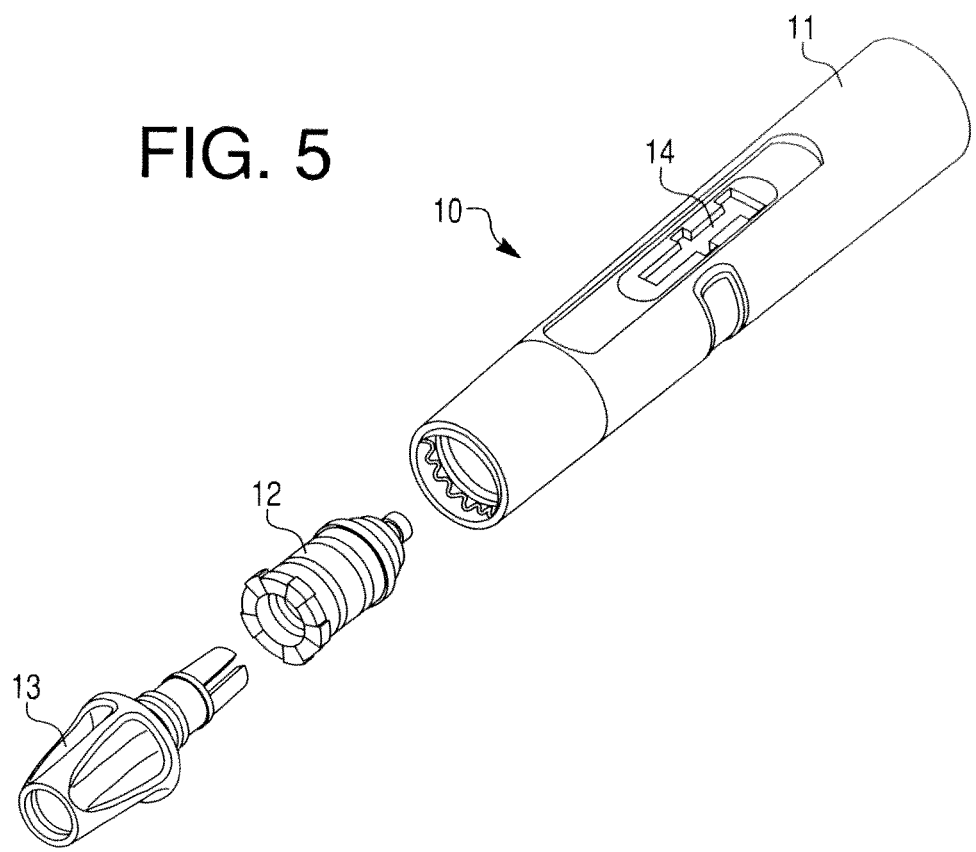

SENSOR GUIDE WIRE ASSEMBLY WITH BUTTON-CELL TYPE BATTERY

BACKGROUND

The present disclosure relates generally to a sensor guide wire assembly and, in particular, to a sensor guide wire assembly having a button-cell type battery.

In many medical procedures, various physiological parameters within the body of a patient are monitored and analyzed. Typically, these parameters are physical in nature—such as pressure, temperature, and flow rate. These parameters are preferably monitored in a safe, reliable and accurate way. For example, a sensor may be mounted on a guide wire and positioned via the guide wire in a blood vessel in a living body to detect a physiological parameter. The sensor includes elements that are directly or indirectly sensitive to the parameter. For example, temperature can be measured by observing the resistance of a conductor having temperature sensitive resistance, as described in U.S. Pat. No. 6,615,067. Another exemplifying sensor may be found in U.S. Pat. No. 6,167,763, in which blood exerts pressure on the sensor which delivers a signal representative of the exerted pressure.

A raw signal generated by the sensor located within the body is transmitted to an external device, in which the signal is translated into physiological data. This data is processed and the results may be continuously saved and/or displayed on, for example, a monitor. In order to power the sensor and communicate signals representing the measured physiological variable to an external device, one or more cables or leads for transmitting the signals are connected to the sensor, and are routed along the guide wire, out from the vessel, and to the external device, conventionally via physical cables. In addition, the guide wire is typically provided with a central metal wire (i.e., a "core wire") serving as a support for the sensor and, optionally, also as an electrical connection to the sensor, and a surrounding tubing. Hence, a sensor guide wire typically comprises a core wire, leads, and a protective tubing, as well as a distal coil or tube and a jacket housing the sensor.

In order to reduce the risks of having an electrically conductive device such as a pressure transducer connected both to a patient and to an electronic monitoring instrument, a wireless arrangement can be used, as described, for example, in US Patent Application Publication No. 2006/0009817. In this publication, the pressure sensor guide wire is configured to be connected, at its proximal end, to a transmitter unit. The transmitter unit is configured to wirelessly communicate via a communication signal with a communication unit that is connected to the external device, in order to transfer measured pressure data to the external device. In addition to the advantage of electrical insulation, a wireless arrangement decreases the amount of cables and other electrical equipment present in an operating room, and also facilitates the use of a standardized communication unit capable of being connected to a wide range of external devices. This obviates the necessity to use a specific external device, possibly different from that which is already present in the operating room. However, in contrast to a conventional sensor guide wire assembly, the pressure sensor in a wireless arrangement is not in electrical connection with the external device. Therefore, an additional energy source is required, such as a battery or capacitor, to power the transmitter unit and the pressure sensor.

SUMMARY

U.S. Patent Publication No. 2009/0124880 describes a sensor guide wire assembly having a detachable energy source (e.g., a battery pack or battery holder). While this assembly provides benefits over previous assemblies, the use of a separate battery pack or battery holder can increase the size and/or complexity of the assembly, and can require additional sterilization of the battery pack or battery holder. Thus, there is a need for improved sensor guide wire assemblies that allow for wireless transmission of sensor data.

The entire contents of the patents and publications cited in this disclosure are incorporated herein by reference for the devices and methods disclosed therein related to measurement.

In one embodiment, a device comprises a transmitter unit configured to be connected to a sensor guide wire that is insertable into a patient to measure a physiological or other parameter, the transmitter unit being configured to wirelessly transfer data representing the measured physiological parameter to a communication unit, and the transmitter unit comprising: a housing, a printed circuit board holder disposed in the housing, a printed circuit board disposed in the housing and held by the printed circuit board holder, the printed circuit board comprising a plurality of electrical contacts, a slider that is slidable from a location outside the housing, the slider including a protrusion extending into an area inside the housing, and a space within the housing, the space being configured to hold one or more batteries. The slider is slidable from a first position, at which a micro-switch is not activated, to a second position, at which the micro-switch is activated by the protrusion of the slider, which allows power to be provided to the printed circuit board.

In one aspect, the space within the housing is configured to hold one or more button-cell type batteries.

In one aspect, the housing comprises at least one member configured to secure the sensor guide wire to the housing.

In one aspect, the device further comprises an end cap configured to secure the one or more batteries inside of the housing.

In one aspect, the device further comprises a spring located between the one or more batteries and the end cap to promote contact between the one or more batteries and at least one of the electrical contacts on the printed circuit board.

In one aspect, the end cap is attached by threads, screws, snaps, or barbs.

In one aspect, the outer surface of the slider is ribbed.

In one aspect, the physiological parameter is pressure, temperature, or flow.

In one aspect, the device further comprises a receiver module to form a transceiver unit.

In one aspect, the device further comprises a sensor guide wire configured to be inserted into a patient to measure a physiological parameter.

In one aspect, the transmitter unit is adapted to communicate by a radio frequency signal with a communication unit, arranged in connection with an external device.

In one aspect, the protrusion is offset from the center of the slider.

In one aspect, the housing has an opening through which the protrusion extends.

In one aspect, the printed circuit board holder has an opening through which the protrusion extends.

In one aspect, the micro-switch is activated by the protrusion being slid over the micro-switch to a position past the micro-switch.

In one aspect, the micro-switch is activated by the protrusion being slid to a position above the micro-switch.

In one aspect, the space within the housing is configured to hold one or more batteries in a position where the longitudinal axis of the one or more batteries is aligned with the longitudinal axis of the housing.

In one aspect, the space within the housing configured to hold one or more batteries is located between the printed circuit board and the end cap.

BRIEF DESCRIPTION OF DRAWINGS

FIG. 2A is a side exploded perspective view of transmitter unit according to one embodiments of the present invention.

FIG. 5 is a side perspective exploded view of a housing of the transmitter unit of FIG. 2A, according to one embodiment of the invention.

DETAILED DESCRIPTION

In the following description, for purposes of explanation and not limitation, details and descriptions are set forth in order to provide a thorough understanding of embodiments of the present invention. However, it will be apparent to those skilled in the art that the present invention may be practiced in other embodiments that depart from these details and descriptions.

Figure 1:
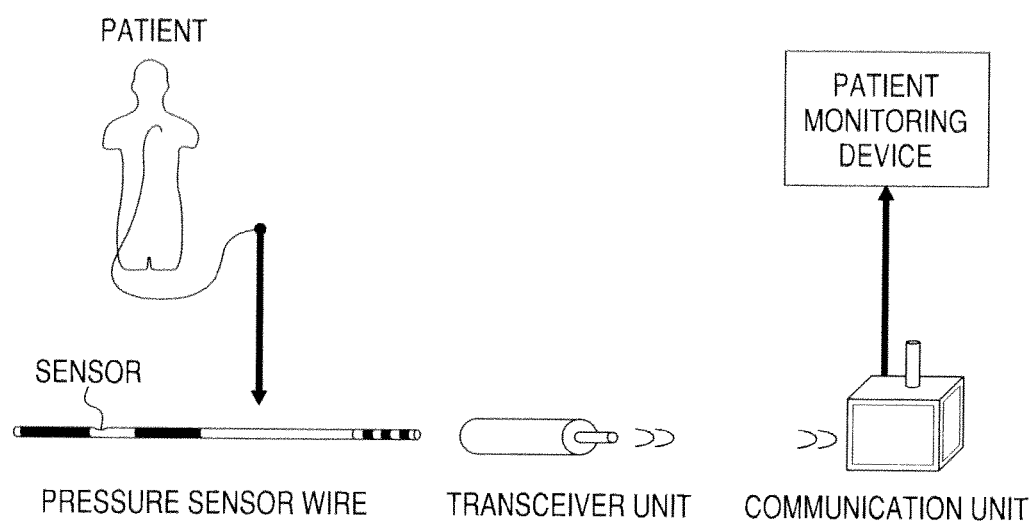
FIG. 1 depicts a system in which a transmitter unit according to embodiments of the present invention can be used.

FIG. 1 depicts a system in which a transmitter unit according to embodiments of the present invention can be used. The system includes a sensor guide wire or pressure sensor wire with a sensor adapted to measure a physiological parameter (e.g., pressure, temperature, or flow) or other parameter inside a patient, and to provide data representing the measured parameter to an external device. The sensor is located at a distal end portion of the sensor guide wire and at least one conductor is configured to conduct an electrical sensor signal from the sensor at the distal end portion of the sensor guide wire to a proximal end portion of the sensor guide wire. The sensor guide wire is adapted to be connected, at its proximal end, to a transmitter unit adapted to wirelessly communicate via a radio frequency signal with a communication unit arranged in connection with an external device, in order to transfer data representing the measured parameter to the external device for analysis and/or display. The data is communicated by the transceiver unit and transferred as a data stream to the communication unit at a prescribed frequency range (in the case where the communication signal is a radio frequency signal). The signal can also be an infrared signal, a light signal, an ultrasound signal or any wirelessly transmitted signal. Preferably, the transmitter unit comprises a sensor signal adapting circuitry and a communication module, connected to the sensor signal adapting circuitry, configured to handle the wireless communication with the communication unit via an antenna.

The external device may be a dedicated device or a patient monitoring device, preferably provided with a monitor, or a PC provided with relevant software and external connections to receive and to process the received data.

Figure 2B:
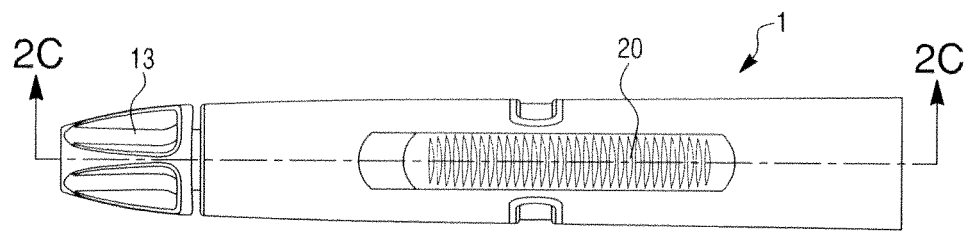
FIG. 2B is a top view of the transmitter unit shown in FIG. 2A.
Figure 2C:
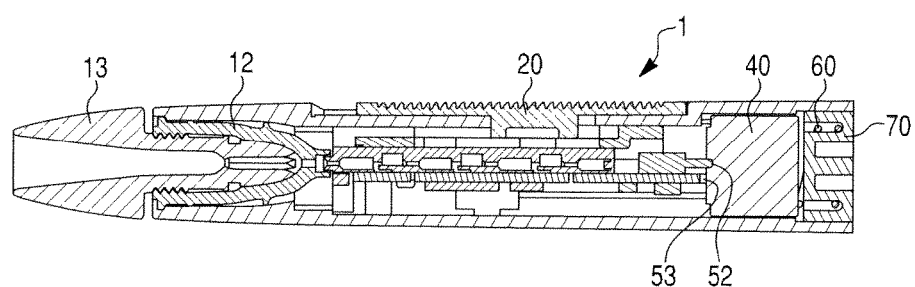
FIG. 2C is a side, cross-sectional view of the transmitter unit shown in FIG. 2A.

FIGS. 2A-2C show the transmitter unit 1 according to one embodiment of the present invention. As shown in FIG. 2A the transmitter unit 1 comprises a housing 10, a slider 20, a printed circuit board holder 30, a battery 40, a printed circuit board 50, a spring 60, and an end cap 70. The printed circuit board 50 includes a plurality of contacts—in this case, a positive potential 52 and a negative potential 53. The battery 40 is a button-cell type battery that is pressed against the positive potential 52 and the negative potential 53 of the printed circuit board assembly 50 by the spring 60 that is held inside of the housing assembly 10 by the end cap 70. The battery 40 is positioned between the printed circuit board assembly 50 and the end cap 70. The spring 60 is configured to promote contact between the battery 40 and the contacts 52, 53 on the printed circuit board 50. The transmitter unit 1 can be turned on and off through use of the slider 20 to activate a micro-switch 51.

As seen in FIG. 5, the housing 10 may include a housing body 11, a cone 12, and a cap 13. The cone 12 and cap 13 may be used to secure a sensor guide wire to the housing, and inhibit the sensor guide wire from detaching from the printed circuit board 50 (as seen in FIG. 2A). The housing assembly 10 may be made of plastic molded pieces. The housing assembly 10 is designed to contain the other components of the transmitter unit 1 as seen in FIG. 2C. The housing body 11 has an opening 14 through which a slider protrusion 21 can extend. The opening 14 also has space in which a slider guide 22 is engaged, as seen in FIG. 2A. The housing body 11 has internal ribs 15 used to secure the end cap 70. The end cap 70 has external ribs 71 to secure it to the housing body 11. By securing the end cap 70 to the housing body 11, the other components can be secured inside of the transmitter unit. The housing body 11 is configured so that the battery 40 may be disposed inside of the housing body 11 such that the battery 40 may be easily removed and replaced. The housing body 11 is configured to house the battery 40 between the printed circuit board 30 and the end cap 70.

Figure 4A:
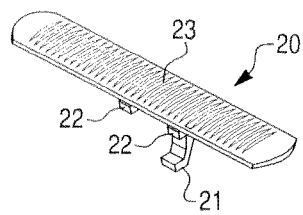
FIG. 4A is a top, side perspective view of a slider of the transmitter unit of FIG. 2A, according to one embodiment of the invention.
Figure 4D:
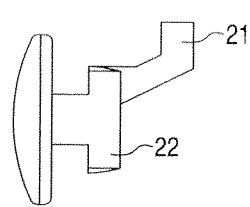
FIG. 4D is a left side view of the slider shown in FIG. 4A.
Figure 4E:
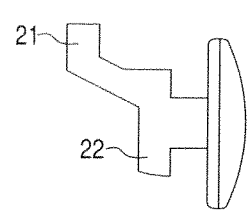
FIG. 4E is a right side view of the slider shown in FIG. 4A.
Figure 4B:
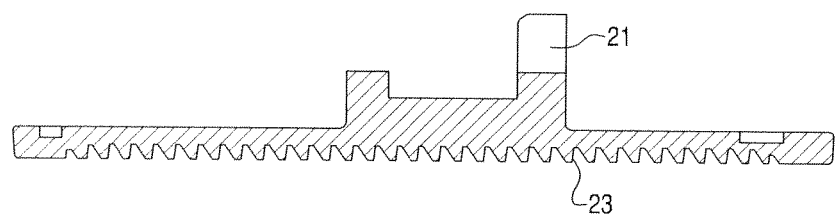
FIG. 4B is a side, cross-sectional view of the slider shown in FIG. 4A.
Figure 4C:
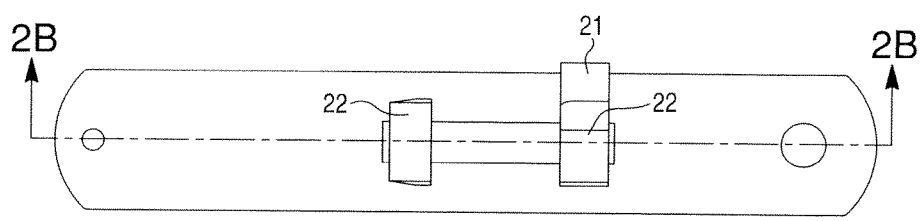
FIG. 4C is a bottom view of the slider shown in FIG. 4A.

As seen in FIGS. 4A-4E, the slider 20 has the protrusion 21. The protrusion 21 is used to activate the micro-switch 51 on the printed circuit board 50 (as seen in FIG. 2A). The protrusion 21 may be offset from a longitudinal center plane of the slider 20 as seen in FIG. 4D, in order to activate the micro-switch 51 that is offset from a longitudinal center plane of the printed circuit board 50. The slider 20 also has the slider guide 22 configured to keep the slider 20 attached to the housing body 11 and guide the slider 20 through the housing opening 14. This will allow the protrusion 21 to be aligned with the micro-switch 51. This alignment allows the protrusion 21 to be able to activate the micro-switch. Additionally, the slider has a ribbed surface 23 configured to facilitate the sliding of the slider 20 by a user.

Figure 6A:
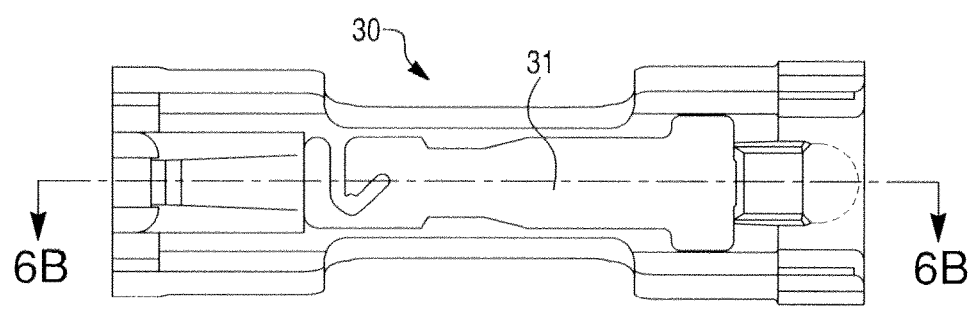
FIG. 6A is a top view of a printed circuit board holder that is included in the transmitter unit of FIG. 2A, according to one embodiment of the invention.
Figure 6B:
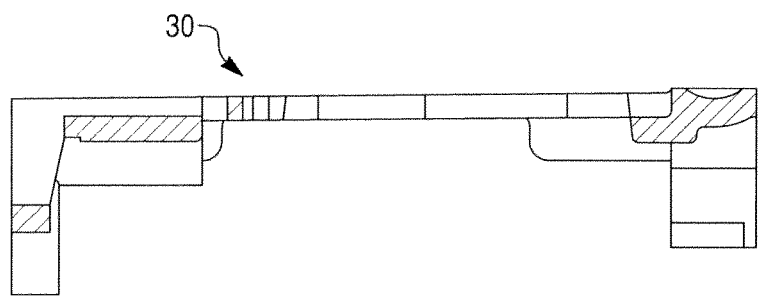
FIG. 6B is a side view of the printed circuit board holder shown in FIG. 6A.

As seen in FIGS. 6A and 6B, the printed circuit board holder 30 is configured to hold the printed circuit board assembly 50. The printed circuit board holder 30 has an opening 31 through which the protrusion 21 extends.

Figure 3:
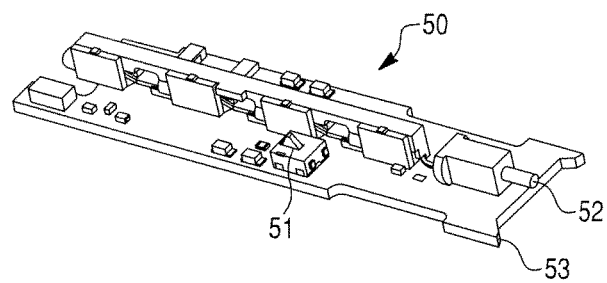
FIG. 3 is a top, side perspective view of a printed circuit board assembly that is included in the transmitter unit of FIG. 2A, according to one embodiment of the invention.

As seen in FIG. 3 the printed circuit board assembly 50 comprises the micro-switch 51, the positive potential 52, and the negative potential 53. The micro-switch 51 is a switch that may be activated by the protrusion 21 being slid over the switch to a position past the switch or a switch that may be activated by the protrusion being slid to a position above the switch. The micro-switch is used to turn the transmitter unit 1 on and off. The micro-switch 51 is located offset from the longitudinal center plane in order to interact with the protrusion 21 which is offset from the longitudinal center plane. The positive potential 52 and negative potential 53 are designed to contact the battery 40.

A transmitter unit with a battery contained inside the unit and a micro-switch allows the unit to be prepared ahead of time but only turned on when necessary by moving the slider to activate the micro-switch. This design also allows the sterilization process of the device to be less time consuming as compared to those that have a separate battery pack that must be sterilized separately. Additionally, containing all of the components within one unit reduces the size and complexity of the device. Finally, the battery may be replaced so that the transmitter unit is reusable.

In some embodiments, the transmitter unit includes a receiver unit. In this case, the unit is, in fact a transceiver unit, such that communication with the external device may be two-way communication.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of components, methods, apparatus, modules, systems, and computer program products.

What is claimed is:

1. A device comprising:
   a transmitter unit configured to be connected to a sensor guide wire that is insertable into a patient to measure a parameter, the transmitter unit being configured to wirelessly transfer data representing the measured parameter to a communication unit, and the transmitter unit comprising:
   a housing,
   a printed circuit board holder disposed in the housing,
   a printed circuit board disposed in the housing and held by the printed circuit board holder, the printed circuit board comprising a plurality of electrical contacts,
   a slider that is slidable from a location outside the housing, the slider including a protrusion extending into an area inside the housing, and
   a space within the housing, the space being configured to hold one or more batteries,
   wherein the slider is slidable from a first position, at which a micro-switch is not activated, to a second position, at which the micro-switch is activated by the protrusion of the slider.

2. The device of claim 1, wherein the space within the housing is configured to hold one or more button-cell type batteries.

3. The device of claim 1, wherein the housing comprises at least one member configured to secure the sensor guide wire to the housing.

4. The device of claim 1, further comprising an end cap configured to secure the one or more batteries inside of the housing.

5. The device of claim 4, further comprising a spring located between the one or more batteries and the end cap to promote contact between the one or more batteries and at least one of the electrical contacts on the printed circuit board.

6. The device of claim 4, wherein the end cap is attached by threads, screws, snaps, or barbs.

7. The device of claim 1, wherein the outer surface of the slider is ribbed.

8. The device of claim 1, wherein the parameter is pressure, temperature, or flow.

9. The device of claim 1, further comprising a receiver module to form a transceiver unit.

10. The device of claim 1, further comprising a sensor guide wire configured to be inserted into the patient to measure a physiological parameter.

11. The device of claim 1, wherein the transmitter unit is adapted to communicate by a radio frequency signal with the communication unit, arranged in connection with an external device.

12. The device of claim 1, wherein the protrusion is offset from the center of the slider.

13. The device of claim 1, wherein the housing has an opening through which the protrusion extends.

14. The device of claim 1, wherein the printed circuit board holder has an opening through which the protrusion extends.

15. The device of claim 1, wherein the micro-switch is activated by the protrusion being slid over the micro-switch to a position past the micro-switch.

16. The device of claim 1, wherein the micro-switch is activated by the protrusion being slid to a position above the micro-switch.

17. The device of claim 1, wherein the space within the housing is configured to hold one or more batteries in a position where a longitudinal axis of the one or more batteries is aligned with a longitudinal axis of the housing.

18. The device of claim 4, wherein the space within the housing configured to hold one or more batteries is located between the printed circuit board and the end cap.

* * * * *